United States Patent [19]
Shim

[11] 3,933,696
[45] Jan. 20, 1976

[54] POLYALKYLENE GLYCOL POLY-PHOSPHORUS COMPOUNDS IN POLYURETHANE FOAMS

[75] Inventor: Kyung Sup Shim, Irvington, N.Y.

[73] Assignee: Stauffer Chemical Company, Westport, Conn.

[22] Filed: July 22, 1974

[21] Appl. No.: 490,525

Related U.S. Application Data

[62] Division of Ser. No. 198,006, Nov. 11, 1971, Pat. No. 3,840,622.

[52] U.S. Cl. .................. 260/2.5 AR; 260/2.5 AS
[51] Int. Cl.² .................. C08G 18/14; C08G 18/50
[58] Field of Search... 260/2.5 AR, 2.5 AJ, 77.5 AR

[56] References Cited
UNITED STATES PATENTS

| | | | |
|---|---|---|---|
| 3,159,605 | 12/1964 | Friedman | 260/929 |
| 3,354,241 | 11/1967 | Larrison | 260/77.5 AR |
| 3,517,090 | 6/1970 | Friedman | 260/77.5 AR |
| 3,578,731 | 5/1971 | Mange | 260/929 |
| 3,798,290 | 3/1974 | Shim | 260/2.5 AR |
| 3,819,750 | 6/1974 | Shim | 260/2.5 AR |
| 3,840,622 | 10/1974 | Shim | 260/929 |
| 3,862,275 | 1/1975 | Shim | 260/2.5 AJ |

*Primary Examiner*—Donald E. Czaja
*Assistant Examiner*—C. Warren Ivy

[57] ABSTRACT

Polyalkylene glycol polyphosphorus compounds having allylic group or aromatic methylene group phosphonate linkages or both phosphite and allylic groups or aromatic methylene group phosphonate linkages are provided by reacting certain polyalkylene or glycol polyphosphites with a stoichiometric or less than a stoichiometric amount of an allylic group containing halide or halomethylated aromatic compound.

7 Claims, No Drawings

POLYALKYLENE GLYCOL POLY-PHOSPHORUS COMPOUNDS IN POLYURETHANE FOAMS

This is a divisional application of Ser. No. 198,006, filed Nov. 11, 1971, now U.S. Pat. No. 3,840,622, dated Oct. 8, 1974.

BACKGROUND OF THE INVENTION

This invention relates to certain polyalkylene polyphosphorus compounds and more particularly to polyalkylene glycol polyphosphorus compounds having allylic group or aromatic methylene group phosphonate linkages and useful as flame retardants.

In the polyurethane field, increased interest is being shown in compounds which can be added to the polyurethane polymers to act as fire retardant agents. Particular interest is being shown in compounds which have functional groups reactive with the polyol or polyisocyanate used in preparing the polyurethane so that the fire retardant agent can be copolymerized into the polymer chain. One such group of reactive flame retardants are the polyalkylene glycol phosphites such as those described in U.S. Pat. No. 3,009,939. However, these materials, due to their high OH numbers and crosslinking tendency, are unsuitable for use in flexible urethane foams. In U.S. Pat. Nos. 3,081,331 and 3,142,651 there is disclosed a method of forming polyalkylene glycol polyphosphites having up to 10 phosphite groups in the polymer chain by reacting a trialkyl phosphite with a polypropylene glycol in a molar ratio of 2.1 to 2.5 moles of glycol per mole of phosphite. These materials are also unsuitable for use in flexible urethane foams as a result of their high OH numbers and their tendency to crosslink.

Another attempt at employing reactive flame retardants, described in U.S. Pat. Nos. 3,142,651 and 3,092,651, involves the use of polypropylene glycol poly-hydrogenphosphonates produced by a thermal polymerization. Likewise, polyalkylene glycol hydrogen polyphosphonates have also been produced by transesterifying a secondary hydrogen phosphonate with a polyalkylene glycol according to the procedure outlined in British Patent Nos. 796,446 and 1,011,118. However, many of these materials have relatively high acidity, causing them to react with and thereby deactivate certain catalyst systems generally used in the formation of polyurethane polymers such, for example, as tertiary amine compounds. The first method has the additional drawback of contamination of the product by the alkylene glycol by-product which contamination is not easily removed.

In order to increase the flame retardancy of some of the above described phosphorus compounds, which have low phosphorus content, the prior art has attempted to incorporate various halogen containing substituents into the above described molecules. Thus, U.S. Pat. No. 3,159,605 describes the reaction of halogenated methanes with these compounds. Likewise, U.S. Pat. Nos. 3,131,206 and 3,328,493 describe the reaction of chloral with them. However, these materials, like their precursors, have many drawbacks. In particular, these products have high OH numbers and low phosphorus content thereby rendering them unsuitable as flame retardants in flexible urethane foams.

In co-pending U.S. applications Ser. No. 86,313, filed Nov. 2, 1970, now U.S. Pat. No. 3,819,750, dated June 25, 1974, and Ser. No. 63,262, filed Aug. 6, 1970, now abandoned, by Kyung Sup Shim, there are disclosed novel polyalkylene glycol vinyl phosphates which are far superior as flame retardants for urethane foams, particularly flexible foam, than any of the above described flame retardants. These vinyl phosphates, however, have one drawback. While they yield foams having excellent flame retardance and physical characteristics, they tend to discolor the center of the bun, thereby rendering the foam objectionable in appearance.

SUMMARY OF THE INVENTION

Accordingly, it is one object of the present invention to provide novel polyalkylene glycol polyphosphorus compounds suitable as flame retardants.

Another object of this invention is to provide polyalkylene glycol polyphosphorus compounds suitable as flame retardants for urethane foams, and in particular, for flexible urethane foams.

A further object of the present invention is to prepare polyalkylene glycol polyphosphorus compounds which exhibit superior flame retardancy and physical properties such as stability, in comparison with the prior art compounds and further yield foams having good color and appearance throughout.

A still further object of the present invention is to provide urethane foams having incorporated therein these novel polyalkylene glycol polyphosphorus compounds.

These and other objects are accomplished herein by providing polyalkylene glycol polyphosphorus compounds having allylic group or aromatic methylene group phosphonate linkages or both phosphite and allylic group or aromatic methylene group phosphonate linkages.

DESCRIPTION OF THE PREFERRED EMBODIMENTS

It has now been discovered that, by reacting an allylic group containing halide or halomethylated aromatic compound with certain polyalkylene glycol polyphosphites in stoichiometric or less than stoichiometric amounts, there is obtained a polyalkylene glycol polyphosphorus compound having allylic group or aromatic methylene group phosphonate linkages or both phosphite and allylic group or aromatic methylene group phosphonate linkages, along the polymer chain. These polyphosphorus polymers are characterized by low OH numbers and low acidity, a lack of the tendency to gel initially or crosslink in the final foamed product, and a high stability during and subsequent to the foam forming process.

The polyphosphorus compounds of the present invention can be represented by an idealized formula as follows:

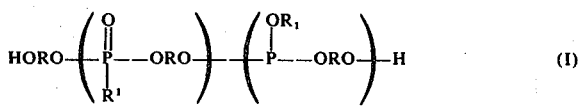

(I)

wherein R is a polyalkylene glycol residue; $R_1$ is an alkyl residue from the tertiary phosphite used to produce the polyalkylene glycol alkyl polyphosphite starting material of the present invention to be discussed hereinafter; $R^1$ is an allylic residue or aromatic methylene residue to be discussed hereinafter; m is a number in the range between from 0 to about 25 and n is a number in the range between from 1 to about 25 such that the sum of $m + n$ is from about 2 to about 50 and preferably between about 4 to about 10. The term alkyl residue as designated by $R_1$ is preferably $C_1$–$C_{10}$ alkyl and most preferably methyl or ethyl. The term polyalkylene glycol residue, designated by R, is meant to define that portion remaining after two hydroxyl groups have been removed from a glycol having the formula:

$$HO—(R''O)_x—H \qquad \text{II.}$$

wherein R'' is an alkylene group of from 2 to about 20 carbon atoms, which is straight chained, branch chained, or a mixture thereof, and $x$ designates the number of repeating alkylene ether units and is normally from 2 to about 20.

The compounds of the present invention are prepared by reacting an allylic group containing halide compound or a halomethylated aromatic compound with a polyalkylene glycol alkyl polyphosphite which has an idealized formula as follows:

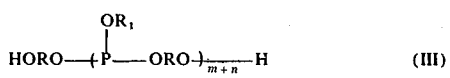
(III)

wherein R, $R_1$, $m$ and $n$ are as defined above. This polyphosphite of formula III in turn, is formed by transesterifying a tertiary phosphite with a polyalkylene glycol in a molar ratio of from about 1 to about 1.5 and preferably from 1 to 1.2 moles of phosphite per mole of glycol.

The tertiary phosphite used to prepare the polyalkylene glycol akyl polyphosphite starting material of formula III has the general formula:

(IV)

wherein each $R_1$ is as defined above. Suitable phosphites include for example, trimethyl phosphite, triethyl phosphate, tripropyl phosphite, tributyl phosphite, trioctyl phosphite, dimethyl ethyl phosphite, diethyl methyl phosphite and the like. Trimethyl and triethyl phosphite are particularly preferred, with trimethyl phosphite being most preferred.

As stated above, the tertiary phosphite of Formula IV above is transesterified with a glycol corresponding to Formula II above to yield the starting polyalkylene glycol alkyl polyphosphite of formula III. Illustrative of the glycols which can be employed in the present invention include the following: diethylene glycol, triethylene glycol, dipropylene glycol, tripropylene glycol, tributylene glycol, polyethylene glycols wherein the average number of ether units is 2, polypropylene glycols wherein the average number of ether units is 14, trihexylene glycol, and the like. Particular preferred glycols are triethylene glycol, dipropylene glycol and tripropylene glycol. It is understood that these propylene glycols can be primary, secondary, or mixtures thereof.

In order to form the polyphosphite starting materials of the present invention represented by Formula III the tertiary phosphite and the desired glycol must be reacted in critical proportions. Thus, the tertiary phosphite should be present in an amount from about 1 to about 1.5 moles per mole of glycol. The preferred range for this preparation is from about 1 to about 1.2 moles of phosphite per mole of glycol. If the glycol is reacted in quantities greater than 1:1 with the phosphite, the product will contain primarily the undesirable mono, di, tri and tetraphosphites and, more importantly, will have a substantial amount of free hydroxyl groups attached to the phosphite group.

The above disclosed transesterification reaction is normally conducted by mixing the phosphite and glycol in the presence of any of the well known transesterification catalysts. Particularly useful catalysts are the alkali metal alcoholates and phenolates such as sodium methylate, sodium decylate, sodium phenolate, tertiary alkylamine, and the like. These catalysts are normally employed in an amount from about 0.01 to about 10 percent, by weight, of the entire reactant mixture. The reaction temperature should initially be kept below the boiling point of the lowest boiling reactant in order to avoid the loss of that reactant. Although the reaction can be conducted at room temperature, i.e., 20° C., it is preferred to conduct it as close to the upper limit as possible in order to increase the rate of reaction. Thus, in the case where trimethyl phosphite is employed as the tertiary phosphite, the reaction temperature is preferably within the range of 80° C. to 100° C. and should not be allowed to rise above 105° C. until at least one R' group on each of the phosphite molecules has been replaced with a polyalkylene glycol. This can normally be determined by monitoring the amount of methanol which has been evolved.

While the reaction can be run to completion at these temperature ranges, it has been found to be advantageous to raise the temperature after this initial replacement of one of the R' groups on the starting phosphite up to a limit of about 200° C. and most preferably up to about 150° C. As stated above, the point at which the temperature should be raised can be determined by monitoring the amount of by-product alkanol produced. Thus, when one mole of trimethyl phosphite is being transesterified, the reaction temperature can be raised after one mole of methanol has been evolved. The transesterification is completed when two moles of methanol have been evolved. The degree of polymerization of the polyphosphite can be controlled to an extent by varying the time of the reaction. Furthermore, the polymer length can be monitored by measuring the viscosity buildup during the reaction according to well known techniques.

The transesterification reaction can optionally be carried out in the presence of an inert solvent, however, such solvent is not required for the practice of the present invention. The term inert solvent is meant to designate any solvent which does not react with the starting materials or products of the present invention. Suitable solvents include the alkylated benzenes such as ethyl benzene, diethyl benzene, toluene, the xylenes, and the like.

The polyphosphite of Formula III produced by the process described above is then reacted with a stoichiometric (or excess) or less than a stoichiometric amount of an organic compound containing an α-halo-β-ethylenic unsaturated group. Compounds of this nature which are encompassed within the scope of this invention correspond to the following formulae V and VI:

(V)

wherein X is halogen, such as chlorine and bromine, $R_2$, $R_3$, $R_4$, $R_5$ and $R_6$ are the same or different and are hydrogen, halogen, alkyl, halo-alkyl, aryl, halo-aryl, aralkyl, or halo-aralkyl and wherein $R_5$ and $R_6$ also may form a cyclic ring of up to 4 carbons; and

(VI)

wherein $R_2$, $R_3$ and X are as defined above and $R_7$ is aryl, such as phenyl, naphthyl and the like, halo-aryl and alkyl-aryl. $R_2$, $R_3$, $R_4$, $R_5$ and $R_6$ are preferably hydrogen or $C_1$-$C_5$ lower alkyl or halo $C_1$-$C_5$ lower alkyl.

The compounds within the scope of Formula V above are further defined herein as allylic group containing halide compounds while the compounds within the scope of Formula VI are defined herein as halomethylated aromatic compounds. Accordingly, the terms allylic residue and aromatic methylene residue as employed in Formula I above to describe R' are meant to be that portion of Formula V and Formula VI remaining after the removal of X. Thus, when R' is an allylic residue, the polyphosphorus compounds of the present invention correspond to the following formula:

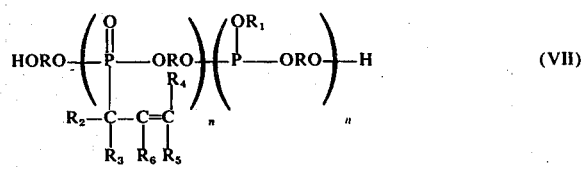

(VII)

wherein R, $R_1$, $R_2$, $R_3$, $R_4$, $R_5$ and $m$ and $n$ are as defined above. When R' is an aromatic methylene residue the polyphosphorus compounds of the present invention correspond to the following formula:

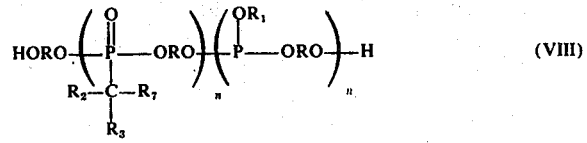

(VIII)

wherein R, $R_1$, $R_2$, $R_3$, $R_7$ and $m$ and $n$ are as defined above.

It will be understood that when difunctional allylic halide group compounds encompassed within Formula V, such as 1,4-dichlorobutene-2, are employed, the final product will be cross-linked to a certain degree.

Further illustrative of compounds within the scope of Formula V include for example, allyl chloride, allyl bromide, 3,4-dichlorobutene-1, 1,2,3-trichloropropene and the like. Allyl chloride and allyl bromide are particularly preferred. Compounds within the scope of Formula VI include for example, benzyl chloride, benzyl bromide, chloromethylnaphthalene, and the like.

The allylic halide compounds of Formula V and the halomethylated aromatic compounds of Formula VI above are reacted with the polyphosphites of Formula III above in either stoichiometric or less than stoichiometric amounts. The term "stoichiometric amount" as used herein, is meant to designate the molar equivalent of phosphite groups in the polyphosphite. Thus, by employing less than this amount, the product will contain unreacted phosphite groups and correspond to compounds within Formula I above wherein $m$ is 1 or more and $n$ is as defined above. By employing a stoichiometric amount, or excess of an allylic halide or halo-methylated aromatic compound, compounds corresponding to Formula I wherein $m$ is o and $n$ is as defined above are produced. Accordingly, if the products resulting from the utilization of less than a stoichiometric amount of halide are desired, any amount of halide less than a stoichiometric amount may be employed. Generally, the desired range for most foam applications of the final product is from about 0.1 to about 0.9 moles of halide compound per mole of phosphite group. On the other hand, if the products resulting from the use of a stoichiometric amount or excess of halide are desired, any substantially stoichiometric or excess quantity of halide may be utilized.

The allylic halide or halomethylated aromatic compound can be reacted with the polyphosphite over a wide temperature range. Normally temperatures from about 50° to about 200° C. are employed. The reaction can be monitored by determining the amount of alkyl halide by-product formed. Thus, when 0.6 molar equivalents or 1.0 molar equivalents of allylic halide compound or halomethylated aromatic compound are used, the reaction is completed when 0.6 moles or 1.0 moles, respectively, of alkyl halide have evolved.

Since the reaction with the allylic halide or halomethylated aromatic compound and the polyphosphite of the present invention is normally endothermic in nature, said reaction is generally performed without the aid of a solvent or diluent as a temperature controlling measure. However, if the use of a solvent or diluent is desired, it should be non-reactive with respect to both the starting materials and desired products and should be miscible therewith. Illustrative of suitable solvents are halobenzenes, such as dichlorobenzene, xylene, ethylbenzene, diethylbenzene, various alkanes and the like.

The novel compounds of the present invention are characterized by their ability to copolymerize with polyisocyanates employed in forming polyurethanes, by their relatively low OH numbers and acidity, by their high phosphorus content, and by their high flame retardancy and stabilizing characteristics in the final foams. These compounds can completely replace the polyols normally employed in forming the foams or they can be used in combination with the polyols, thereby yielding foams with greatly improved flame resistance. Since they react in the foam forming process, their residues are chemically bonded into the foam, thereby giving them high permanance, even upon high temperature aging. The acid numbers of the compounds of the present invention are normally below about 2 milligrams of KOH per gram of the polyalkylene glycol polyphosphorus compound. This low acidity makes these compounds relatively unreactive toward the polymerization catalysts employed in producing the polyurethane foams. As mentioned above, these compounds have relatively low OH numbers as compared to the prior art flame retardants and therefore, can be used in flexible urethane foams without materially affecting the physical properties of such foams. By the term relatively low OH numbers, it is meant to designate OH numbers below about 160 and preferably below 100.

The compounds of the present invention are further characterized by the fact that they are substantially linear polymers when compared to those disclosed in the prior art. This result, at least in part is from the fact that the intermediate polyalkylene glycol alkyl polyphosphites used to make the present compounds contain primarily alkyl side chains attached to the phosphite groups. Consequently, the labile halogen released by the attacking allylic halide or halomethylated aromatic compound will preferentially react with the alkyl side chain rather than with the glycol linking groups. Thus, it has been observed that the by-product formed by the addition of the allylic halide or halomethylated aromatic compound to the polyphosphite intermediates used herein is the alkyl halide rather than the halogenated polyether alcohol which would result from attack on the glycol. Since the phosphite alkyl group is attacked preferentially there is little or no depolymerization.

An additional advantage inherent in the present invention is the fact that the alkyl halide by-product can easily be separated from the desired final product whereas a halogenated polyether alcohol by-product, such as would be formed when using the polymers described in the prior art cannot be easily separated due to its higher boiling point. Furthermore, the necessity for separating a halogenated polyether alcohol by-product is manifest since it is a monofunctional alcohol which would seriously impair, if not destroy, the foam forming ability of the urethane foam mix.

The compounds of the present invention, when employed in sufficient quantity, will yield a self-extinguishing polyurethane foam. This characteristic is particularly important in the area of flexible foams due to the wide use of such foams in hospitals, homes and automobiles. Normally, the compounds of the present invention can be employed in amounts of from about 5 to about 30 percent, by weight, of the entire foam forming mixture to yield self-extinguishing flexible foams. Preferably, they are employed in amounts from 10 to 15 percent, by weight, of the entire mixture. It is understood, however, that this amount will vary depending upon the particular foam being used, and that the required proportions can easily be determined with a minimum amount of blending work.

While the polyphosphorus compounds of the present invention are primarily intended for use in urethane foams, it is contemplated that they can also be used in a wide variety of polymeric systems. Illustrative of these systems are: polyesters, polyolefins, cellulose ethers and esters, urethane coatings and elastomers, polymethyl methacrylates, polyvinyl chlorides, and many others. Furthermore, the compounds of the present invention can also be employed in combination with any of the known flame retardants in foams or polymeric systems.

The polyurethane foams within which the flame retardants described above are incorporated are well known in the art. They are produced by the reaction of a di- or polyisocyanate and a di- or polyhydroxy (polyol) compound in the presence of a blowing agent and a catalyst. The foams can be made by any of the basic techniques used in foam formation; i.e., the prepolymer technique, the semi-prepolymer technique or the one-shot process. These techniques are well known and described in the polyurethane art.

As examples of organic di- and polyisocyanates which can be employed to make the polyurethane foams there can be employed toluene-2,4-diisocyanate, toluene-2,6-diisocyanate; 4-methoxy-1,3-phenylene diisocyanate; diphenyl methane-4,4'-diisocyanate; 4-chloro-1,3-phenylene-diisocyanate; 4-isopropyl-1,3-phenylene-diisocyanate; 4-ethoxy-1,3-phenylene-diisocyanate; 2,4-diisocyanate-diphenylether; 3,3'-dimethyl-4,4'diisocyanateodiphenyl methane; mesitylene diisocyanate; durylene diisocyanate; 4,4'-methylene-bis (phenylisocyanate); benzidine diisocyanate; o-nitrobenzidine diisocyanate; 4,4'-diisocyanate-dibenzyl; 3,3'-bitolylene-4,4'-diisocyanate; 1,5-naphthalene diisocyanate; tetramethylene diisocyanate; hexamethylene diisocyanate; decamethylene diisocyanate; toluene-2,4,6-triisocyanate; tritolylmethane triisocyanate; 2,4,4'-triisocyanatodiphenyl ether; the reaction product of toluene diisocyanate with trimethylolpropane; and the reaction product of toluene diisocyanate with 1,2,6-hexanetriol.

Alternatively, as the polyisocyanate there can be used prepolymers made by reacting one or more of the above polyisocyanates with a di- or polyhydroxy compound such as a polyester having terminal hydroxyl groups, a polyhydric alcohol, glycerides or hydroxy containing glycerides, etc. These prepolymers should have terminal isocyanate groups and, to insure their presence, it is frequently desirable to employ an excess of 5% or more of the polyisocyanate in forming the prepolymer. Typical examples of such prepolymers having isocyanate end groups are those formed from toluene diisocyanate and polyhydroxy compounds. In most cases, a mixture of 80% of the 2,4-isomer and 20% of the 2,6-isomer of toluene diisocyanate is employed in making these prepolymers. Thus, there can be used the prepolymers resulting from the reaction between toluene diisocyanate and caster oil, blown tung oil, blown linseed oil or blown soya oil, and of toluene diisocyanate and the polyester of ethylene glycol, propylene glycol and adipic acid.

Examples of suitable polyols are polyethylene glycol, polypropylene glycols, ethylene glycol, diethylene glycol, triethylene glycol, propylene glycol, dipropylene glycol, tripropylene glycol, 1,4-butanediol, thiodiglycol, glycerol, trimethylolethane, trimethylol propane, ether triols from glycerine and propylene oxide, other containing triols from 1,2,6-hexanetriol and propylene oxide, sorbitol-propylene oxide adducts, pentaerythritol-propylene oxide adducts, trimethylol phenol, oxypropylated sucrose, triethanolamine, pentacrythritol, diethanolamine, castor oil, blown linseed oil, blown soya oil, N,N,N',N'-tetrakis(2-hydroxyethyl) ethylenediamine, N,N,N',N'-tetrakis(2-hydroxypropyl)ethylenediamine, N,N,N',N'',N'', -pentakis(2-hydroxypropyl) diethyl triamine, N,N,N',N'',N'''-pentakis(2-hydroxyethyl) diethylene triamine, mixed ethylene glycol-propylene glycol adipate resin, polyethylene adipate phthalate and polyneopentylene sebacate.

In preparing the foamed polyurethanes there can be used any of the conventional basic catalysts such, for example, as N-methyl morpholine, N-ethyl morpholine, 1,2,4-trimethylpiperazine, trimethyl amine, triethyl amine, tributyl amine and other trialkyl amines, the esterification product of adipic acid and diethyletha-nolamine, triethyl amine citrate, 3-morpholinopropionamide, 1,4-bis(2-hydroxypropyl)-2-methylpiperazine, 2-diethylaminoacetamide, 3-diethylaminopropionamide, diethylethanolamine, triethylenediamine, N,N,N',N'-tetrakis (2-hydroxypropyl) ethylenediamine, N,N'-dimethylpiperazine, N,N-dimethylhexahydroaniline, tribenzylamine and sodium phenolate. Also applicable are tin compounds, e.g., hydrocarbon tin acrylates such as dibutyltin dilaurate, dibutyltin diacetate, dibutyltin dioctoate, tributyltin monolaurate, dimethyltin diacetate, dioctyltin diacetate, dilauryltin diacetate, dibutyltin maleate, hydrocarbon tin alkoxides, e.g., dibutyltin diethoxide, dibutyltin dimethoxide, diethyltin dibutoxide as well as other tin compounds, e.g., octylstannoic acid, trimethyltin hydroxide, trimethyltin chloride, triphenyltin hydroxide, trimethyltin chloride, triphenyltin hydride, triallyltin chloride, trioctyltin fluoride, dibutyltin dibromide, bis-(carboethoxymethyl) tin diiodide, tributyltin chloride, trioctyltin acetate, butyltin trichloride, octyltin tris-(thiobutoxide), dimethyltin oxide, dibutyl tin oxide, dioctyltin oxide, diphenyltin oxide, stannous octanoate, and stannous oleate.

Any of the conventional surfactants can be used in amounts of 1% or less, e.g. 0.2% by weight of the composition. The preferred surfactants are silicones, e.g., polydimethyl siloxane having a viscosity of 3 to 100 centistokes, triethoxydimethyl polysiloxane, molecular weight 850 copolymerized with a dimethoxypolyethylene glycol having a molecular weight of 750.

The foaming reaction can be carried out by adding water to the polyol prior to or simultaneously with the addition of the polyisocyanate. Alternatively, foams can be prepared by the use of a foaming or blowing agent. These are usually a liquefied, halogen substituted alkane such, for example, as methylene chloride. Especially preferred are those halogen substituted alkanes having at least one fluorine atom in their molecules such as trichlorofluoromethane, dichlorodifluoromethane dichloromonofluoromethane, chlorodifluoromethane, dichlorotetrafluoroethane. In using these blowing agents, they are uniformly distributed in either the polyol reactant or the polyisocyanate reactant whereupon the reactants are mixed permitting the temperature of the mixture to rise during the ensuing reaction above the boiling point of the liquefied gas so as to produce a porous polyurethane. It should be noted that foaming may also be affected by combining the use of a flowing agent with the addition of water to the polyol.

Having generally described the invention, the following examples are given for purposes of illustration. It will be understood that the invention is not limited to these examples but is susceptible to different modifications that will be recognized by one of ordinary skill in the art.

EXAMPLE 1

A three-necked flask equipped with a mechanical stirrer, thermometer, and condenser is charged with 545 g. (4.4 mole of trimethyl phosphite, 536 g. (4.0 mole) of dipropylene glycol (1.0 mole) and 1.0 g. of sodium methoxide. The reactants are then heated to 105° C. under a nitrogen gas atmosphere over a period of 5 hours during which time 185 g. of methanol is collected. The reaction is completed under aspirator pressure for an additional 2 hours. Then, 250 g. benzene followed by 582 g. (4.0 moles) of 1,2,3-trichloropropene is added to the reaction mixture and heated for 12 hours to a temperature of 113° C. After removal of the volatile components, 849 g. of a viscous colorless oil product are obtained.

Analysis:
Acid No. = 0.28 mg KOH/g
OH number = 19 mg KOH/g
% P = 10.8

Infrared analysis shows a multiplet centered at 1600 cm$^{-1}$.

EXAMPLE 2

A three-necked flask equipped with a mechanical stirrer, thermometer, and condenser is charged with 134 g. (1 mole) of dipropylene glycol, 124 g. (1 mole) trimethyl phosphite and 0.3 g. of sodium methoxide. The reactants are heated to 100° C. in a $N_2$ atmosphere for 4 hours while removing methanol. The reaction is completed under aspirator pressure for an additional 3 hours. Finally, 100 g. (1.3 moles) of allyl chloride is introduced to the reaction mixture and heated to a reflux temperature of 65° C. for 2 days. The excess and unreacted allyl chloride is then removed followed by the removal of the remaining volatiles at 140° C. under aspirator pressure to leave 183 g. of the liquid oily product.

Analysis:
Acidity = neutral
OH number = 50 mg KOH/g.
% P = 13.5

Infrared analysis of the product indicates a band at 1645 cm$^{-1}$.

EXAMPLE 3

A three-necked 3 liter flask equipped with a mechanical stirrer, thermometer, a distilling head is charged with 545 g. (4.4 mole) trimethyl phosphite, 536 g. (4 mole) dipropylene glycol and 1.0 g. of sodium methoxide. These reactants are then heated to between 100° – 110° C. for 2 hours during which time 248 g. of methanol is distilled out. This initial reaction is completed by continued heating at 100° C. under aspirator pressure for an additional 3 hours. 500 g. (4 mole) of 3,4-dichlorobutene-1 is introduced to the reaction product and heated at 120° C. for 20 hours. After removal of the volatile components 626 g. of final product is obtained.

Analysis:
Acid No. = 0.56 mg. KOH/g. sample
OH number = 12 mg KOH/g
% P = 13.4

Infrared analysis shows band at 1630 cm$^{-1}$.

EXAMPLE 4

A three-necked 500 ml. flask equipped with a mechanical stirrer, thermometer, and condenser is charged with 100 grams (0.52 mole) of the reaction product of dipropylene glycol and trimethylphosphite in a 1 to 1.1 mole ratio respectively. 65 grams (0.34 mole) of benzyl chloride is added to the flask and the resulting mixture is heated to about 110° to 115° C. over a period of 3.5 hours. The volatiles are removed at 105° C. under reduced pressure and 110 grams of slightly cloudy colorless liquid product are obtained.

Analysis: Acid No. = neutral

In like manner to the above examples, good results are obtained when tripropylene glycol is substituted for the dipropylene glycol as well as when allyl bromide is substituted for the allyl chloride in Examples 1 and 2.

EXAMPLE 5

Flexible polyurethane foams are prepared by employing the following formulations:

| | I | II |
|---|---|---|
| Propoxylated glycerol (3000 mol. wt.) | 200 g. | 200 g. |
| poly(dipropylene glycol allyl phosphonate) | | |
| Prepared according to Example 2 | 30 g. | 30 g. |
| FYROL HB 32 (tris[2,3-dibromopropyl]phosphate) | 0 g. | 10 g. |
| Water | 8.0 g. | 8.0 g. |
| Silicone Surfactant | 1.8 g. | 1.8 g. |
| N-ethyl morpholine | 0.45 g. | 0.45 g. |
| Dimethylaminoethyl ether | 0.35 g. | 0.35 g. |
| Methylene Chloride | 6.0 g. | 6.0 g. |
| Stannous Octoate, 50% in dioctyl phthalate | 0.65 g. | 0.65 g. |
| Toluene diisocyanate (80/20 isomers) | 104.8 g. | 104.8 g. |
| Properties | | |
| Rise-time | 127 sec. | 130 sec. |
| Color-forming tendency | good | good |
| Density | 1.49 lbs/ft.³ | 1.62 lbs/ft. |
| Flammability, ASTMD 1692 | self-extinguishing | self-ext. |
| burn extent | 3.4 inches | 2.0 inches |
| extinguishment time | 48 seconds | 34 seconds |
| Dry Heat (22 hours at 140° C.) | | |
| flammability | self-extinguishing | self-ext. |
| burn extent | 3.1 inches | 1.1 inches |
| extinguishment time | 37 seconds | 19 seconds |

Obviously, numerous modifications and variations of the present invention are possible in the light of the above teachings. It is, therefore, to be understood that within the scope of the appended claims the invention may be practiced otherwise than as specifically described herein.

What is claimed is:

1. A flame retardant polyurethane foam containing as a chemically bonded integral part thereof the residue of a polyphosphorus compound having the formula:

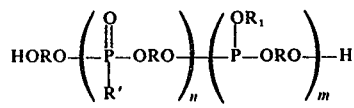

wherein R is a polyalkylene glycol residue defined as that portion remaining after two hydroxyl groups have been removed from a glycol having the formula:

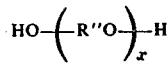

wherein R'' is an alkylene group of from 2 to about 20 carbon atoms, which is straight chain, branch chain, or a mixture thereof, and X designates the number of repeating alkylene ether units and is from 2 to about 20; $R_1$ is a $C_1$–$C_{10}$ alkyl residue; R' is an allylic residue formed from a compound selected from the group consisting of allyl bromide, allyl chloride, 3,4-dichlorobutene-1, 1,2,3-trichloropropene and 1,4-dichlorobutene-2; m is a number in the range from 0 to about 25; and n is a number in the range from 1 to about 25 with the proviso that the sum of m+n is in the range of from about 2 to about 50.

2. The polyurethane foam of claim 1 wherein said residue of the polyphosphorus compound is present in an amount of from about 5 to about 30 percent by weight of the entire foam.

3. The polyurethane foam of claim 2 wherein R is a residue of a polyalkylene glycol selected from the group consisting of diethylene glycol, triethylene glycol, dipropylene glycol and tripropylene glycol; $R_1$ is methyl and R' is selected from the group consisting of

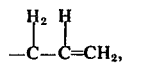

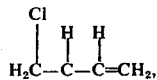

and

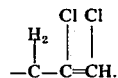

4. The polyurethane foam of claim 3 wherein R is a residue of dipropylene glycol, R' is

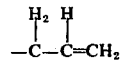

and $R_1$ is methyl.

5. The polyurethane foam of claim 4 wherein m is 0.

6. The polyurethane foam of claim 1 wherein R is a residue of a polyalkylene glycol selected from the group consisting of diethylene glycol, triethylene glycol, dipropylene glycol, tripropylene glycol, tributylene glycol and trihexylene glycol.

7. The polyurethane foam of claim 1 wherein m is 0.

* * * * *

UNITED STATES PATENT AND TRADEMARK OFFICE
CERTIFICATE OF CORRECTION

PATENT NO. : 3,933,696
DATED : January 20, 1976
INVENTOR(S) : Kyung S. Shim

It is certified that error appears in the above-identified patent and that said Letters Patent are hereby corrected as shown below:

Col. 2, lines 55-60, change formula I to read:

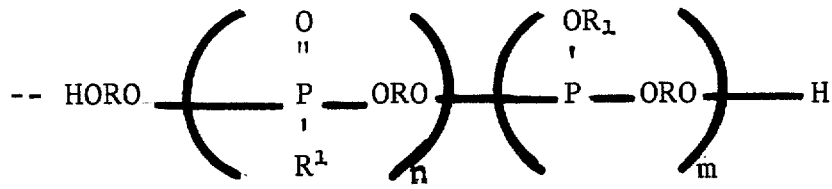

Col. 3, line 41, change "phosphate" after "ethyl" to -- phosphite --;

Col. 5, lines 6-11, change formula (VI) to read:

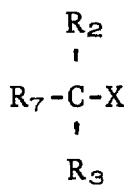

Col. 5, lines 30-36 and 42-47, change the second subscript at the right hand side of formulae (VII) and (VIII) from "n" to -- m --;

Col. 11, in the Table, left hand column, change "Properties" to -- _Properties_ --; and

UNITED STATES PATENT AND TRADEMARK OFFICE
CERTIFICATE OF CORRECTION

PATENT NO. : 3,933,696  
DATED : January 20, 1976  
INVENTOR(S) : Kyung S. Shim

Page 2 of 2

It is certified that error appears in the above-identified patent and that said Letters Patent are hereby corrected as shown below:

Col. 12, lines 32-34, change the formula to read:

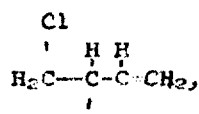

Signed and Sealed this

First Day of February 1977

[SEAL]

*Attest:*

RUTH C. MASON  
*Attesting Officer*

C. MARSHALL DANN  
*Commissioner of Patents and Trademarks*